United States Patent
Sarka et al.

(10) Patent No.: US 12,350,072 B2
(45) Date of Patent: Jul. 8, 2025

(54) METHOD, APPARATUS, SYSTEM AND COMPUTER PROGRAM FOR PROCESSING AN ALMOST-PERIODIC INPUT SIGNAL

(71) Applicant: Sony Corporation, Tokyo (JP)

(72) Inventors: Paulius Sarka, Basingstoke (GB);
Serkan Eryilmaz, Basingstoke (GB);
Joana Dries, Basingstoke (GB);
Gonzalo Bailador, Basingstoke (GB)

(73) Assignee: Sony Corporation, Tokyo (JP)

( * ) Notice: Subject to any disclaimer, the term of this patent is extended or adjusted under 35 U.S.C. 154(b) by 285 days.

(21) Appl. No.: 17/184,602

(22) Filed: Feb. 25, 2021

(65) Prior Publication Data
US 2021/0275106 A1    Sep. 9, 2021

(30) Foreign Application Priority Data

Mar. 6, 2020 (EP) .................................. 20161534

(51) Int. Cl.
*A61B 5/00* (2006.01)
*A61B 5/026* (2006.01)
(Continued)

(52) U.S. Cl.
CPC .......... *A61B 5/7232* (2013.01); *A61B 5/0261* (2013.01); *A61B 5/11* (2013.01); *A61B 5/346* (2021.01); *A61B 5/372* (2021.01); *A61B 5/7425* (2013.01); *G16H 40/67* (2018.01); *G16H 50/30* (2018.01)

(58) Field of Classification Search
CPC ....... A61B 5/7232; A61B 5/346; A61B 5/372; A61B 5/0261; A61B 5/11; A61B 5/7425; G16H 40/67; G16H 50/30
See application file for complete search history.

(56) References Cited

U.S. PATENT DOCUMENTS

| 2004/0015894 A1 | 1/2004 | Lange |
| 2004/0054297 A1 | 3/2004 | Wingeier et al. |

(Continued)

FOREIGN PATENT DOCUMENTS

WO   WO-2014047472 A1 *  3/2014  ......... A61B 5/04012

OTHER PUBLICATIONS

Hedayat Abrishami, P-QRS-T Localization in ECG Using Deep Learning, IEEE EMBS International Conference on Biomedical & Health Informatics (Year: 2018).*

(Continued)

*Primary Examiner* — Rochelle D Turchen
(74) *Attorney, Agent, or Firm* — XSENSUS LLP

(57) ABSTRACT

Examples relate to a method, an apparatus and a computer program for processing an almost-periodic input signal comprising a plurality of signal portions of varying duration, and to a system comprising such an apparatus and a visual output device. The plurality of signal portions are characterized by a common signal shape. The method comprises assigning the plurality of signal portions to a plurality of sets of signal portions. Each set of signal portions comprises two or more signal portions. The method comprises adjusting a duration of at least a subset of the signal portions such that the signal portions of a set have the same duration. The method comprises superimposing the two or more signal portions of a set within a combined output signal.

20 Claims, 5 Drawing Sheets

(51) Int. Cl.
*A61B 5/11* (2006.01)
*A61B 5/346* (2021.01)
*A61B 5/372* (2021.01)
*G16H 40/67* (2018.01)
*G16H 50/30* (2018.01)

(56) References Cited

U.S. PATENT DOCUMENTS

2011/0159467 A1    6/2011  Peot et al.
2012/0296569 A1   11/2012  Shahaf et al.
2014/0194758 A1*   7/2014  Korenberg ............. A61B 6/032
                                                           600/509

OTHER PUBLICATIONS

Qazi et al., "Single Trial EEG Patterns for the Prediction of Individual Differences in Fluid Intelligence", Frontiers in Human Neuroscience, vol. 10, Article 687, Jan. 20, 2017, pp. 1-19.

* cited by examiner

METHOD, APPARATUS, SYSTEM AND COMPUTER PROGRAM FOR PROCESSING AN ALMOST-PERIODIC INPUT SIGNAL

CROSS-REFERENCE TO RELATED APPLICATION

This application claims priority from EP 20161534.1, filed on Mar. 6, 2020, the contents of which are incorporated by reference herein in its entirety.

FIELD

Examples relate to a method, an apparatus and a computer program for processing an almost-periodic input signal, and to a system comprising such an apparatus and a visual output device.

BACKGROUND

The processing of sensor data is a field of research and development. For example, the rise of low-cost biometric sensors enables new applications that rely on the processing of biometric sensor data. At the same time, sensor data of such sensors is often measured over a long time, e.g. while a user carries a smartwatch comprising a biometric sensor, or while the user wears headphones comprising a biometric sensor.

SUMMARY

There may be a desire for providing a concept which provides an improved processing of sensor data that is collected over a long timeframe.

Various embodiments of the present disclosure are based on the finding that sensor data, e.g. sensor data from biometric sensors, often is almost-periodic, as a common signal shape (e.g. a heart rhythm, a gait pattern etc.) is repeated over and over in the sensor data, with varying duration and potentially with other variations. For example, an Electroencephalographical (EEG) signal comprises a common signal shape that is repeated over and over (with some variations) and which indicates the activity of the brain of a user being probed. While the user performs a same specific task, e.g. while the user reads a book, or drives a car, the variations of the signal shape are often sufficiently small for some time period, so that the EEG signal can be considered as an almost-periodic signal. At the same time, the changes within the signal are so minute that they are difficult to visualize. Embodiments of the present disclosure use the almost-periodic property to provide a concept for processing such input signals that enables a more meaningful representation of such signals, while losing none or little of its information content.

Embodiments of the present disclosure provide a method for processing an almost-periodic input signal comprising a plurality of signal portions of varying duration. The plurality of signal portions are characterized by a common signal shape. The method comprises assigning the plurality of signal portions to a plurality of sets of signal portions. Each set of signal portions comprises two or more signal portions. The method comprises adjusting a duration of at least a subset of the signal portions such that the signal portions of a set have the same dura-tion. The method comprises superimposing the two or more signal portions of a set within a combined output signal. By assigning the signal portions to different sets, they may be selected to be output concurrently within the combined output signal. By adjusting the duration of at least some of the signal portions, they may properly align with each other in the combined output signal. By superimposing the signal portions within the combined output signal, a representation of a long input signal is enabled that is compact (and thus can be shown in a meaningful manner on a visual display device) without losing (much of) its information content.

In various embodiments, the signal portions of a set occur sequentially within the input signal. Thus, the chronological order of sets of signal portions may be retained within the combined output signal.

In some embodiments, the adjusted duration of the signal portions may be the same for the plurality of signal portions. This may provide a better representation of the signal shape, which is less influenced by the variations in the duration of the signal portions.

Alternatively, the sets of signal portions may comprise at least a first set and a second set, and the signal portions of the first set may have an adjusted duration being different from an adjusted duration of the signal portions of the second set. This may illustrate the variations in the duration of the signal portions.

For example, the adjusted duration of the signal portions of a set is based on an average of the durations of the signal portions of the set. Thus, the duration of the signal portions of the set may be indicative of the durations of members of the set.

In some embodiments, a fixed number of subsequent signal portions is assigned to the same set. This may facilitate the processing of the input signal.

In various embodiments, the duration of at least the subset of signal portions is adjusted based on a result of a loss function. The loss function may be based on a difference between dura-tion-adjusted versions of the signal portions. In other words, the signal portions may be transformed to obtain the adjusted duration of the signal portions in such a manner, that a result of the loss function is reduced compared to other transformation.

For example, machine-learning may be used to vary one or more input parameters of the loss function in order to improve the result of the loss function. In other words, machine-learning may be used to determine, how the signal portions are to be transformed in order to achieve an improved result when using the loss function.

In at least some embodiments, the input signal may be a continuous input signal. For example, biometric sensor data is often continuous. Embodiments may be used to provide a more meaningful representation of continuous input signals, as the superimposition of multiple signal portions enables a slower update speed of the combined output signal.

The adjustment of the duration of the at least subset of the signal portions may be based on a portion of the continuous input signal having a pre-defined duration. In other words, the input signal may be broken down into portions, and within the portion of the input signal, signal portions may be identified, and their duration may be adjusted. Thus, the method may be applied to continuous input signals.

In various embodiments, the combined output signal comprises, for each set, the individual signal portions and an average of the signal portions of the set. For example, the average (or mean) of the signal portions may provide an overview of the set (which shows the signal shape, and in which noise may be reduced), while the underlying signal portions are still present.

The combined output signal may be provided to a visual output device. Embodiments may thus provide an improved visual representation of the input signal, which may improve an intelligibility of the input signal.

For example, the combined output signal may be configured such that the two or more signal portions of a set are shown superimposed over each other on the visual output device. Thus, a longer portion of the input signal may be shown at the same time without compressing the visual representation of the input signal.

In some embodiments, the combined output signal is configured such that an average of the signal portions of the set is shown superimposed over the individual signal portions on the visual output device. For example, the average (or mean) of the signal portions may provide an overview of the set (which shows the signal shape, and in which noise may be reduced), while the underlying signal portions are still visible.

In some embodiments, the combined output signal is configured such that a sequence of sets of signal portions is shown on the visual output device. The sequence of sets may visualize the chronological order of the sets of signal portions being shown.

In various embodiments, the input signal may be one of an electroencephalogram signal, an electrocardiogram signal and a photoplethysmogram signal. Alternatively, the input signal may represent an inertial recording of human movement. These signals are almost-periodic signals, and are often processed over a longer period of time.

In some embodiments, the method may comprise determining, based on the signal shape or duration of the plurality of signal portions, whether the input signal is quasi-periodic for a portion of the input signal comprising the plurality of signal portions. Subsequent/further processing of the plurality of signal portions of the portion of the input signal may be omitted if the portion of the input signal is not deemed quasi-periodic.

Embodiments of the present disclosure further provide a computer program having a program code for performing the above method, when the computer program is executed on a computer, a processor, or a programmable hardware component.

Embodiments of the present disclosure further provide an apparatus for processing an almost-periodic input signal comprising a plurality of signal portions of varying duration. The plurality of signal portions are characterized by a common signal shape. The apparatus comprises processing circuitry that is configured to obtain the almost-periodic input signal. The processing circuitry is configured to assign the plurality of signal portions to a plurality of sets of signal portions. Each set of signal portions comprises two or more signal portions. The processing circuitry is configured to adjust a duration of at least a subset of the signal portions such that the signal portions of a set have the same duration. The processing circuitry is configured to superimpose the two or more signal portions of a set within a combined output signal.

In some embodiments, the processing circuitry is configured to provide the combined output signal to a visual output device. Embodiments of the present disclosure further provide a system comprising the apparatus and the visual output device. The visual output device may be configured to output a visual representation of the combined output signal.

BRIEF DESCRIPTION OF THE FIGURES

Some examples of apparatuses and/or methods will be described in the following by way of example only, and with reference to the accompanying figures, in which.

DETAILED DESCRIPTION

Various examples will now be described more fully with reference to the accompanying drawings in which some examples are illustrated. In the figures, the thicknesses of lines, layers and/or regions may be exaggerated for clarity.

Accordingly, while further examples are capable of various modifications and alternative forms, some particular examples thereof are shown in the figures and will subsequently be described in detail. However, this detailed description does not limit further examples to the particular forms described. Further examples may cover all modifications, equivalents, and alternatives falling within the scope of the disclosure. Same or like numbers refer to like or similar elements throughout the description of the figures, which may be implemented identically or in modified form when compared to one another while providing for the same or a similar functionality.

It will be understood that when an element is referred to as being "connected" or "coupled" to another element, the elements may be directly connected or coupled via one or more intervening elements. If two elements A and B are combined using an "or", this is to be understood to disclose all possible combinations, i.e. only A, only B as well as A and B, if not explicitly or implicitly defined otherwise. An alternative wording for the same combinations is "at least one of A and B" or "A and/or B". The same applies, mutatis mutandis, for combinations of more than two Elements.

The terminology used herein for the purpose of describing particular examples is not intended to be limiting for further examples. Whenever a singular form such as "a," "an" and "the" is used and using only a single element is neither explicitly or implicitly defined as being mandatory, further examples may also use plural elements to implement the same functionality. Likewise, when a functionality is subsequently described as being implemented using multiple elements, further examples may implement the same functionality using a single element or processing entity. It will be further understood that the terms "comprises," "comprising," "includes" and/or "including," when used, specify the presence of the stated features, integers, steps, operations, processes, acts, elements and/or components, but do not preclude the presence or addition of one or more other features, integers, steps, operations, processes, acts, elements, components and/or any group thereof.

Unless otherwise defined, all terms (including technical and scientific terms) are used herein in their ordinary meaning of the art to which the examples belong.

Figure 1A:
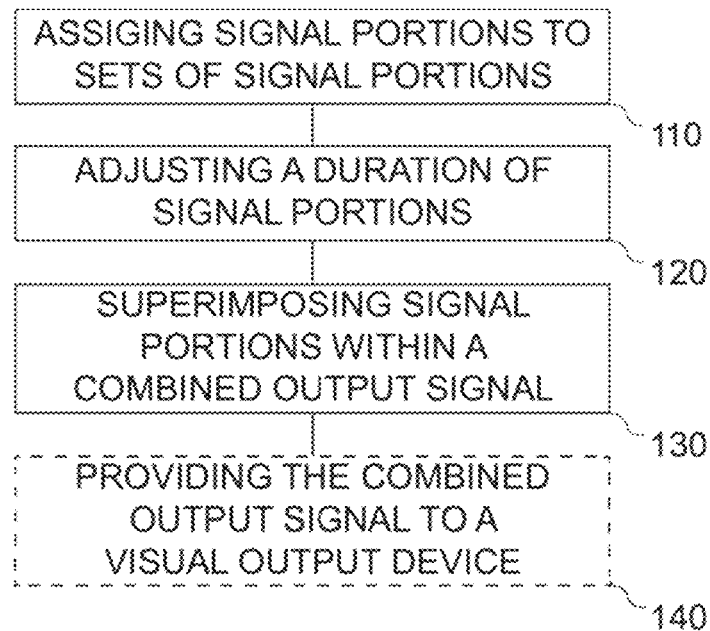
FIG. 1a shows a flow chart of an embodiment of a method for processing an almost-periodic input signal.

FIG. 1a shows a flow chart of an embodiment of a method for processing an almost-periodic input signal. The almost-periodic input signal comprises a plurality of signal portions of varying duration. The plurality of signal portions are characterized by a common signal shape. The method comprises assigning 110 the plurality of signal portions to a plurality of sets of signal portions. Each set of signal portions comprises two or more signal portions. The method comprises adjusting 120 a duration of at least a subset of the signal portions such that the signal portions of a set have the same duration. The method comprises superimposing 130 the two or more signal portions of a set within a combined output signal.

Figure 1B:
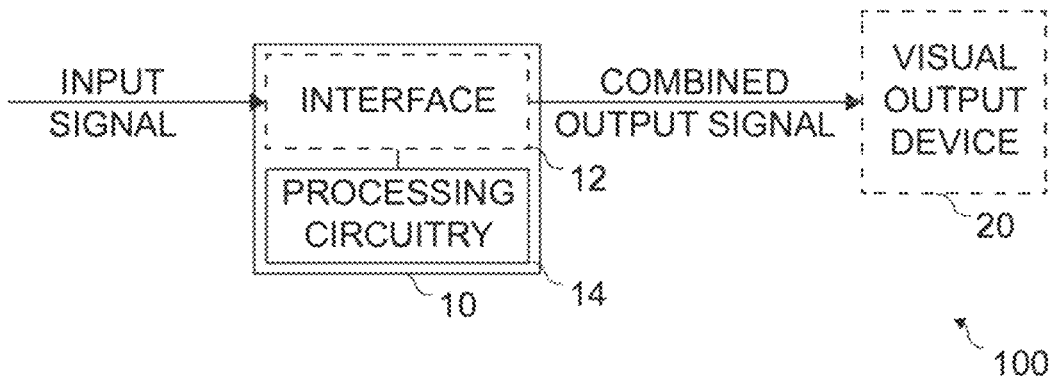
FIG. 1b shows a block diagram of an embodiment of an apparatus for processing an almost-periodic input signal.

FIG. 1b shows a block diagram of an embodiment of a (corresponding) apparatus 10 for processing an almost-periodic input signal. The apparatus 10 comprises processing circuitry 14 and an optional interface 12. In general, the processing circuitry 14 is configured to provide the functionality of the apparatus 10, e.g. in conjunction with the interface 12. The processing circuitry 14 may be configured to perform the method of FIG. 1a. For example, the processing circuitry is configured to obtain the almost-periodic input signal (e.g. via the interface 12). The processing circuitry is configured to assign the plurality of signal portions to the plurality of sets of signal portions. The processing circuitry is configured to adjust the duration of at least the subset of the signal portions such that the signal portions of a set have the same duration. The processing circuitry is configured to superimpose the two or more signal portions of a set within a combined output signal. The processing circuitry may be configured to provide the combined output signal via the interface 12. For example, the processing circuitry may be configured to provide the combined output signal to a visual output device 20. FIG. 1b further shows a system 100 comprising both the apparatus 10 and the visual output device 20. The visual output device may be configured to output a visual representation of the combined output signal.

The following description relates both to the method of FIG. 1a and to the apparatus of FIG. 1b. Features described in connection with the method of FIG. 1a may likewise be applied to the apparatus of FIG. 1b.

Embodiments of the present disclosure relate to a method, an apparatus and a computer program for processing an almost-periodic input signal. In formal terms, an almost-periodic signal can be defined as a one-dimensional time series that can be modelled as a perfect periodic signal with locally warped (locally stretched or locally compressed) time and (optional) additive noise. In some cases, the signal shape (optionally) can also be amplified or dampened. As is evident from the definition, an almost-periodic signal is based on signal portions that are repeated periodically, albeit in a locally stretched or compressed manner, and which exhibit additive noise. These signal portions are based on the same signal shape—i.e. the shape of the signal portions is common to (all of) the signal portions. While the signal shape is common to the signal portions, the signal shape can be locally warped (i.e. distorted) in each of the portions, e.g. stretched or compressed in time. Accordingly, the duration of the signal portions varies, according to the local warping of the signal portions. In other words, the signal portions may have different durations, and even in signal portions of the same length, different local warping of time may be observed. Consequently, the signal portions often are not linearly stretched or compressed, but locally, e.g. such that a compression factor is non-linear over the duration of the respective signal portions. Over time, the signal shape may change, but for the purpose of the present disclosure, the (underlying) signal shape of the plurality of signal portions may be common. In other words, the input signal may be quasi-periodic for stretches of time, e.g. for the combined duration of the plurality of signal portions. The signal shape of the plurality of signal portions may be considered as a common signal shape as long as it does not vary more than a pre-defined threshold, e.g. in terms of the shape of the signal portion and/or in terms of duration of the signal portion. For example, the signal shape of the plurality of signal portions may be considered as a common signal shape if, when the plurality of signal portions are adjusted to the same duration, a mean square error between each signal portion of the plurality of signal portions and an average of the duration-adjusted versions of the signal portions is smaller than a pre-defined threshold for the mean square error, and/or if the duration of each of the signal portions before duration adjustment is at most a time threshold longer or shorter than the average duration of the plurality of signal portions. For example, the time-threshold may either be an absolute time threshold (e.g. 0.5 seconds), or a relative threshold (e.g. 50% of the average duration of the plurality of signal portions).

In some cases, the input signal, which may be a sensor signal, may be almost-periodic during a time-period and not almost-periodic during other time-periods. For example, the input signal may change without exhibiting a common signal shape, e.g. during transitory periods. In this case, the signal shape of the plurality of signal portions may vary more than the pre-defined threshold, and the input signal might not be considered an almost-periodic input signal, at least for the window of time when the pre-defined threshold is violated. The method may accordingly comprise determining whether the input signal comprises an almost-periodic signal at certain time periods (so that it is suitable for the processing according to embodiments). For example, the method may comprise determining whether the input signal is quasi-periodic for a portion of the input signal comprising the plurality of signal portions, based on the signal shape or duration of the plurality of signal portions. Further processing of the plurality of signal portions may be omitted if the input signal is not deemed quasi-periodic during the portion of the input signal comprising the plurality of signal portions. For example, the method may comprise adjusting the duration of the plurality of signal portions to the same duration, and determining the mean square error between each signal portion of the plurality of signal portions and the average of the duration-adjusted versions of the signal portions. The input signal may be deemed quasi-periodic during the portion of the input signal comprising the plurality of signal portions if the mean square error is at most the pre-defined threshold for the mean square error. Alternatively or additionally, the method may comprise calculating an average duration of the plurality of signal portions, and comparing a difference between the (non-duration adjusted) duration of each of the signal portions to the time threshold. The input signal may be deemed quasi-periodic during the portion of the input signal comprising the plurality of signal portions if the duration of each of the signal portions is at most the time threshold longer or shorter than the average duration of the plurality of signal portions.

Processing of the input signal may resume once the pre-defined threshold holds for a subsequent plurality of signal portions, e.g. after the transitory period. After the transitory period, another common signal shape may define the quasi-periodic property of the input signal. In other words, an input signal may be almost-periodic with different underlying signal shapes at different times. For example, the plurality of signal portions may relate to the same set of circumstances, such as the same activity of a user providing a biometric input signal comprising the plurality of signal portions. Once the circumstances change, the underlying signal shape may (slowly) also change. In many cases, the change may be gradual enough so that the input signal can be considered quasi-periodic over the combined duration of the plurality of signal portions.

Such almost-periodic signals can be found in a variety of scenarios. For example, almost-periodic signals are often present in sensor data. In other words, the input signal may be a sensor signal comprising almost-periodic sensor data. For example, the input signal may be a sensor signal of a bio-monitoring sensor (also denoted biometric sensor), i.e. of a sensor for monitoring one or more impulses generated by an organic entity. For example, the bio-monitoring sensor may be a sensor for monitoring one or more impulses generated by a human body. In some embodiments, such bio-monitoring sensors may be sensors for monitoring electrical impulses generated by the human body. For example, the bio-monitoring sensor may be an electroencephalograph (i.e. an electroencephalography sensor, a sensor for sensing electrical impulses generated by the brain) or an electrocardiograph (i.e. an electrocardiography sensor, a sensor for sensing an electrical activity of the heart). Alternatively, the bio-monitoring sensor may be photoplethysmography sensor, i.e. a sensor for sensing blood volume changes, such as a pulse oximeter. Accordingly, the input signal may be one of an electroencephalogram (EEG) signal, an electrocardiogram signal (ECG) and a photoplethysmogram (PPG) signal. Alternatively, the bio-monitoring sensor may be a sensor for recording a (inertial) movement of the human body. For example, the bio-monitoring sensor may be or comprise an accelerometer for recording the (inertial) movement of the human body. Accordingly, the input signal may represent an inertial recording of human movement, e.g. a gait of a human. In any case, the bio-monitoring sensor may be comprised in a wearable device, such as a smartwatch, a fitness tracker, a breast strap sensor, a head band, headphones or a smartphone.

Apart from bio-monitoring sensors, other sensors may be used as well, e.g. vibration sensors attached to a piece of machinery, or the input signal may be derived from an almost-periodic current draw of an electronic circuit or of a piece of machinery.

In any case, the input signal may be monitored and/or processed over a long period of time. In other words, the input signal may be continuously processed. For example, the input signal may be a continuous input signal, i.e. an input signal that is continuously updated. To handle a continuous input signal, the input signal may be processed in a windowed manner. In other words, the method may comprise selecting a portion of the continuous input signal (i.e. "windowing the input signal"), the portion of the continuous input signal comprising the plurality of signal portions. In some embodiments, the portion of the continuous input signal has a pre-defined duration. For example, the portion of the continuous input signal may have a pre-defined number of signal portions, which define the pre-defined duration of the portion of the continuous input signal. Accordingly, the method may comprise detecting the number of signal portions (i.e. counting the signal portions) within the input signal. For example, the detection may be performed based on the common signal shape of the signal portions, e.g. based on a characteristic peak of the common signal shape. In other words, the detection of the number of signal portions may be based on a characteristic peak of the common signal shape. The method may comprise selecting the portion of the continuous input signal based on the detected number of signal portions.

If the plurality of signal portions are not contained in a separated manner within the input signal, they may be identified before they are assigned to the plurality of sets of signal portions. In other words, the method may comprise identifying the plurality of sets of signal portions within the input signal. Again, the common signal shape may be used to identify the plurality of signal portions within the input signal. For example, if the common signal shape comprises a characteristic peak, the characteristic peak may be used to identify the plurality of signal portions within the input signal. For example, the characteristic signal peak may mark the beginning (or end) of a signal portion of the plurality of signal portions. In other words, the characteristic signal peak may separate a preceding signal portion from a subsequent signal portion.

The method comprises assigning 110 the plurality of signal portions to a plurality of sets of signal portions, with each set of signal portions comprising two or more signal portions. This may be done according to a pre-defined assignment scheme, which may be based on the number of signal portions, or based on a duration of the signal portions. For example, a fixed (i.e. pre-defined) number of subsequent signal portions may be assigned to the same set, e.g. two, three, four, five, six or eight signal portions per set. Alternatively, the number of subsequent signal portions that are assigned to the same set may be based on the (average, minimal or maximal) duration of the signal portions. Accordingly, the method may comprise determining the (average, minimal or maximal) duration of the plurality of signal portions. For example, for longer signal portions, a higher number of subsequent signal portions may be included in the same set, and for shorter signal portions, a lower number of subsequent signal portions may be included in the same set. In general, the signal portions of a set may occur (directly) sequentially within the input signal. In other words, the signal portions of a set may be (directly) subsequent signal portions within the input signal.

The method comprises adjusting 120 a duration of at least a subset of the signal portions such that the signal portions of a set have the same duration. There are a variety of different concepts for adjusting the duration such that the signal portions of a set have the same duration. In a simple implementation, the duration of the individual signal portions may be determined, and the duration of at least the subset of the signal portions may be linearly compressed or stretched so that the that the signal portions of the set have the same duration.

In some other embodiments, a more complex approach may be chosen, in which durations of the individual signal portions are not linearly adjusted, but in which the local warping of time within the individual signal portions is taken into account. Such more complex transformations may be performed with the help of a loss function. In embodiments, the duration of at least the subset of signal portions may be adjusted based on a result of a loss function. In general, a loss function (i.e. a cost function) is a function that maps a state onto a number representing a "loss" or "cost" of said state. Optimization algorithms may be used to reduce the "loss" or "cost" by altering the state in a way that reduces the "loss" or "cost". Accordingly, the method may comprise searching for how at least the subset of signal portions are to transformed such that the signal portions of the set have the same duration, and such that the loss function is reduced or minimized (compared to other transformations of the at least the subset signal portions). This concept may be similar to concepts that try to increase a "reward" that can be obtained from a certain state, albeit with an inverse approach. Thus, the "loss function" may be implemented using a "reward function", with the aim of increasing the reward function.

In general, the loss function may be chosen such, that the loss is reduced when the common signal shape overlaps for the signal portions of a set. Accordingly, the loss function may be based on a difference between duration-adjusted versions of the signal portions. For example, the loss function may yield a lower value if the difference between duration-adjusted versions of the signal portions is reduced, and a higher value if the difference between duration-adjusted versions of the signal portions is increased. As the signal portions share a common signal shape, the difference may be based on the two factors that have been introduced above—locally warped time and additive noise (which may be unavoidable). By compensating for the locally warped time, the result of the loss function may be reduced. Accordingly, the method may comprise transforming at least the subset of signal portions such, that the effect of locally warped time is compensated for between the signal portions of a set.

These transformations might not be performed on the signal portions (yet), but they may be performed by altering input parameters of the loss function. In some embodiments, as explained with reference to FIG. 6 in more detail, the loss function may comprise a time warping component that models the local warping of time for at least the subset of signal portions. In connection with FIG. 6, this time warping component is denoted the g function. The time warping component, in turn, may depend on one or more input parameters of the loss function. By varying the one or more input parameters (which may alternatively or additionally control other aspects of the loss function), the local warping of time for at least the subset of signal portions may be adjusted. In general, an optimization or minimization algorithm or approach may be used to identify the one or more input parameters to use in order to reduce the loss function. For example, machine-learning may be used to vary one or more input parameters of the loss function in order to improve the result of the loss function.

In general, machine learning refers to algorithms and statistical models that computer systems may use to perform a specific task without using explicit instructions, instead relying on models and inference. For example, in machine-learning, instead of a rule-based transformation of data, a transformation of data may be used, that is inferred from an analysis of historical and/or training data. Machine-learning algorithms are usually based on a machine-learning model. In other words, the term "machine-learning algorithm" may denote a set of instructions that may be used to create, train or use a machine-learning model. The term "machine-learning model" may denote a data structure and/or set of rules that represents the learned knowledge, e.g. based on the training performed by the machine-learning algorithm.

In embodiments, a category of machine-leaning may be employed that is denoted "gradient descent". Gradient descent is an optimization algorithm that is aimed at finding parameters that minimize a loss function. In the present context, gradient descent may be used to determine the one or more input parameters of the loss function that reduce the result of the loss function. In other words, a gradient descent-based machine-learning algorithm may be used to vary the one or more input parameters of the loss function in order to improve the result of the loss function. In general, gradient descent-based algorithm attempt to determine a derivative of the cost, and vary the parameters in away that promises to reduce the result of the cost function (based on the derivative). The gradient-based machine-learning algorithm may start from an initial set of input parameters (i.e. the one or more input parameters), evaluate the loss function for the set of input parameters, iteratively refine the set of input parameters, re-evaluate the loss function, and keep refining the input parameters until a termination condition is reached. The obtained set of input parameters (i.e. the one or more input parameters) may be used to adjust the duration of at least the subset of signal portions.

Another type of machine-learning algorithm that can be used to identify the one or more input parameters is denoted reinforcement learning. In other words, reinforcement learning may be used to vary the one or more input parameters. In reinforcement learning, one or more software actors (called "software agents") are trained to take actions in an environment. Based on the taken actions, a reward is calculated. Reinforcement learning is based on training the one or more software agents to choose the actions such, that the cumulative reward is increased, leading to software agents that become better at the task they are given (as evidenced by increasing rewards). In the present case, the "reward" may be modeled by the loss function, with a lower result yielded by the loss function providing an increasing reward, and with the one or more input parameters being adjusted by the one or more software agents. Again, the one or more input parameters being provided by the one or more software agents may be used to adjust the duration of at least the subset of signal portions.

In both cases, the adjustment of the duration of the at least subset of the signal portions may be based on a portion of the continuous input signal having a pre-defined duration. As has been introduced above, the pre-defined duration may either be a fixed duration, or may be chosen based on the duration of the signal portions of the set. In other words, the adjustment of the duration of the at least subset of the signal portions may be based on a portion of the continuous input signal comprising the two or more signal portions of the set. For example, the loss function may be calculated for a portion of the portion of the continuous input signal comprising the two or more signal portions of the set. For example, the portion of the continuous input signal may be limited by the duration of the two or more signal portions of the set.

Once the one or more input parameters of the loss function that reduce or minimize the result of the loss function are determined, they may be used to adjust the duration of at least the subset of the signal portions, e.g. to compensate for the local warping of time. In other words, the method may comprise transforming at least the subset of the signal portions based on the one or more input parameters of the loss function to adjust the duration of at least the subset of the signal portions, e.g. in order to counteract (e.g. compensate) the local warping of time present in at least the subset of signal portions. In more general terms, the method may comprise transforming at least the subset of the signal portions to adjust the duration of at least the subset of the signal portions, to counteract the local warping of time present in at least the subset of signal portions.

In general, the adjusted duration of the signal portions of a set is the same. Between sets, different approaches may be chosen. For example, all of the signal portions may be transformed to the same duration. In other words, the adjusted duration of the signal portions may be the same for the plurality of signal portions. For example, the adjusted duration of the signal portions may be a pre-defined (i.e. fixed) duration.

Alternatively, different durations may be used for different sets of signal portions. In more formal terms, the sets of signal portions may comprise at least a first set and a second set. The signal portions of the first set may have an adjusted duration that is different from an adjusted duration of the signal portions of the second set. In other words, the adjusted durations of the signal portions of the first and second set may be different. For example, the adjusted durations of the individual sets of signal portions may be chosen based on the durations of their members. In other words, the adjusted duration of the signal portions of a set may be based on an average of the durations of the signal portions of the set. Accordingly, the method may comprise determining the average of the durations of the signal portions of the set before adjusting the duration of the signal portions of the set, and adjusting the duration of at least the subset of the signal portions of the set to the average of the durations of the signal portions of the set.

The method comprises superimposing 130 the two or more (potentially duration-adjusted) signal portions of a set (on each other, or on an average of the signal portions of the set) within a combined output signal. In this context, the term "superimposed" or "superimposing" is used to describe that the two or more signal portions of a set are overlaid on top of each other such that they share the same coordinate system (e.g. the time axis and the same value axis), with the individual signal portions potentially crossing each other within the coordinate system. In general, different types of combined output signals may be used. For example, the combined output signal may be provided to a subsequent signal processing apparatus that is used to perform further processing on the output signal. Alternatively, the combined output signal may be stored within a memory or storage device, e.g. as a file or as a portion of memory. In some embodiments, however, the combined output signal is provided 140 to a visual output device, e.g. to the visual output device 20, via the interface 12. Accordingly, the combined output signal may be a combined output signal for a visual output signal, comprising visual information. The combined output signal may be configured such that the two or more signal portions of a set are shown superimposed over each other on the visual output device. In other words, the combined output signal may comprise a visual representation of the two or more signal portions of a set being superimposed on each other. For example, the display device may be a display, e.g. a Liquid Crystal Display (LCD), a Mini- or Micro-LED (Light Emitting Diode)-based display or an Organic Light Emitting Diode (OLED)-based display. Alternatively, the display device may be a projection device.

In addition to the superimposed members of the respective set, an average (i.e. mean) of the signal portions of the respective shown may be superimposed within the combined output signal. In other words, the combined output signal may comprise, for each set, the individual signal portions and an average of the signal portions of the set. Accordingly, the method may comprise computing the average (i.e. mean) of the signal portions of each set. The average may also be shown on the visual output device, e.g. superimposed on the individual signal portions of the set, or separate from the individual signal portions. In other words, the combined output signal may be configured such that an average of the signal portions of the set is shown superimposed over the individual signal portions, or separate from the individual signal portions, on the visual output device. If the average is included in the combined output signal, the individual signal portions may be shown with a reduced weighting, e.g. using dashed lines or using a lighter color, than the average.

In general, the sets of signal portions may be provided in sequence within the combined output signal, and the signal portions of a set may be provided superimposed on each other (i.e. concurrently) within the combined input signal. In other words, the combined output signal may be configured such that a sequence of sets of signal portions is shown on the visual output device. For example, the sequence of sets may be a logical sequence that is derived from the presentation, e.g. shown chronologically from left to right on the visual output device if the signal portions are shown without continuous movement. Alternatively, the combined output signal may be configured such that the sequence of sets of signal portions is shown continually moving across the display device, e.g. from right to left.

In addition to the superimposed signal portions, the combined output signal may also comprise a time-line. In various embodiments, the time-line may represent the superimposition of the signal portions in the combined output signal. For example, for each set of signal portions, the combined signal may comprise an indication on the number of signal portions being superimposed per set. An example regarding the output of a time-line can be seen in FIG. 8.

For example, embodiments may be used to monitor an EEG signal of a user, and to present a combined output signal that is based on the EEG signal to the user next to a representation of the user's activity. By showing the EEG signal next to the activity, the user can learn to associate the shape of the signal portions of the EEG signal with the specific activity, which may help the user to draw conclusions, such as "deep work is similar to meditation" or "work is more productive in a non-agitated state". The activity of the user may be derived from the user's calendar, from the user's previous EEG signals, or from sensor data of one or more further sensors of a wearable device being worn by the user. For example, if the input signal is gained from an EEG sensor that is arranged in headphones, the use of the headphones may indicate the user's activity. For example, if the user has used the headphones as a headset, he/she might have conducted a telephone conference. If the headphones are coupled to a gaming console or to a television set playing games, he/she may have been gaming or watching television. If the headphones are used to play mediation music, the user may have been meditating. The user may be presented with the combined output signal next to the determined activity, e.g. via the display device 20. An example of such a presentation is shown in connection with FIG. 5.

The interface 12 may correspond to one or more inputs and/or outputs for receiving and/or transmitting information, which may be in digital (bit) values according to a specified code, within a module, between modules or between modules of different entities. For example, the at least one interface 12 may comprise interface circuitry configured to receive and/or transmit information.

In embodiments the processing circuitry 14 may be implemented using one or more processing units, one or more processing devices, any means for processing, such as a processor, a computer or a programmable hardware component being operable with accordingly adapted software. In other words, the described function of the processing circuitry 14 may as well be implemented in software, which is then executed on one or more programmable hardware components. Such hardware components may comprise a general-purpose processor, a Digital Signal Processor (DSP), a micro-controller, etc. The processing circuitry 14 is coupled to the interface 12.

More details and aspects of the apparatus 10, method, computer program and/or system 100 are mentioned in connection with the proposed concept or one or more examples described above or below (e.g. FIG. 2a to 8). The apparatus 10, method, computer program and/or system 100 may comprise one or more additional optional features corresponding to one or more aspects of the proposed concept or one or more examples described above or below.

Embodiments of the present disclosure relate to a visual representation of an almost-periodic signal. At least some embodiments of the present disclosure provide a meaningful representation of an EEG signal.

Figure 2A:
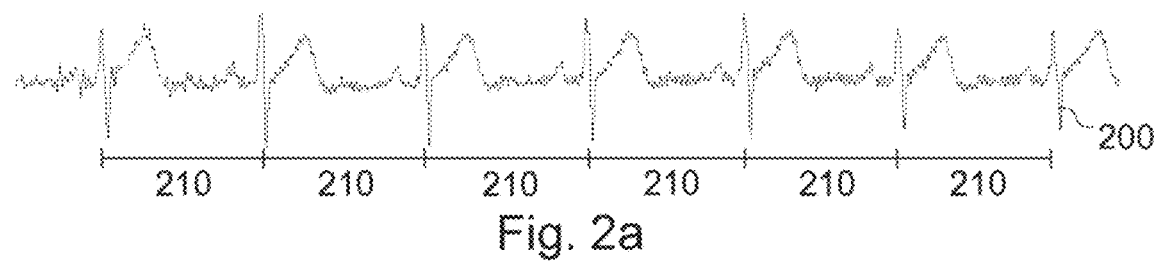
FIGS. 2a to 2d show different visual representations of an almost-periodic signal.

An almost-periodic signal may be defined as a one-dimensional time series that can be modelled as a perfect periodic signal with locally warped (locally stretched or locally compressed) time and additive noise. FIG. 2a shows a visual example of such a signal. FIG. 2a shows an almost-periodic signal 200 having a plurality of signal portions 210 of varying duration.

More precisely, a perfect periodic signal may be a function $f$ that satisfies $f(x+p)=f(x)$ for all $x \in T$ (Time) and some p (called period). A local time warp of size d is denoted a deformation of the time axis by a continuous function g: $T \rightarrow T$, such that $|g(x)-x|<d$, for $x \in T$. Additive noise is a stochastic process $\{n(t)\} t \in T$ such that $n(t)$ are independently and identically distributed (iid) random variables for all $t \in T$. An almost-periodic signal (p, d) is then a function that can be modelled as $aps(x)=f(g(x))+n(x)$.

Examples of almost-periodic signal are readings of physiological sensors, such as EEG (electroencephalogram), ECG (electrocardiogram), PPG (photoplethysmogram), or an inertial recordings of some human movement (walking).

At least some embodiments address the desire of presenting long intervals (e.g. hundreds of periods, i.e. signal portions) of a signal to a user in such a way, that at the same time user may see a.) any part of the interval (e.g. the whole interval) and b.) characteristic details of the period.

Figure 2B:
Figure 2C:
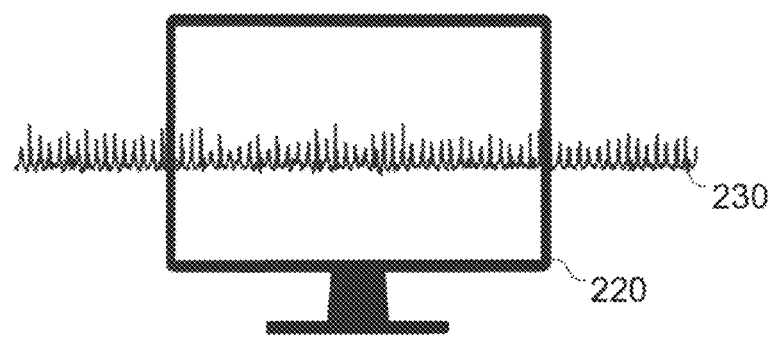

To illustrate the challenges in presenting long intervals, FIGS. 2b and 2c show two approaches for visualizing a selected range of a signal—time-wise compression. In this case, only one of a) or b) may be chosen—either the user can see the detail of the period (e.g. on a screen 220), or the global view. Seeing both at the same time is not possible. If user wants to see the details of the period, only a small section of the signal may be presented to the user, as shown in FIG. 2b. If the user wants to see the full signal (or a large part of it), details of the period may be lost, as shown in FIG. 2c with the time-compressed version 230 of the signal.

Figure 2D:
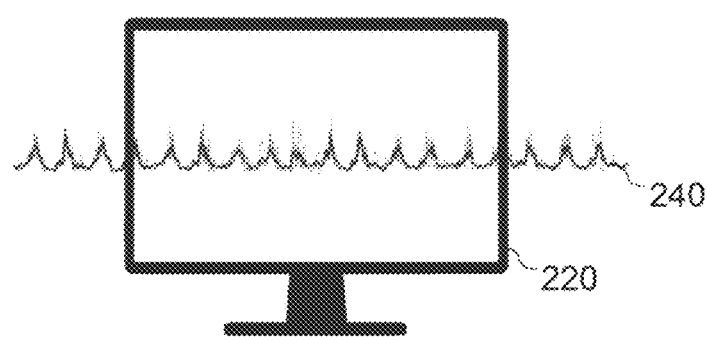

Rather than compressing the signal time-wise, at least some embodiments of the present disclosure propose to locally overlap the signal (e.g. within a combined output signal), making use of the fact that the signal is almost-periodic. In this way, if the user wants to see the full detail of the signal, the same small part of it may be shown, as shown in FIG. 2b. If the user wants to see a larger segment, the neighboring periods (i.e. signal portions) may be overlapped, as shown in FIG. 2d with the overlapped version 240 of the signal.

Figure 3A:
FIGS. 3a to 3d show different visual representations of an almost-periodic signal, in which different numbers of signals are being overlapped.
Figure 3B:
Figure 3C:
Figure 3D:

Overlapping may be implemented by taking two neighboring periods and displaying them on top of each other. This process can be repeated multiple times, resulting in a signal representation that is shorter by half for each repetition, as shown in FIGS. 3a to 3d. FIGS. 3a to 3d show different visual representations of an almost-periodic signal, in which different numbers of signals are being overlapped In FIG. 3a, the original signal is shown. In FIG. 3b, the overlapping is performed once, resulting in a signal that is half as long as the original signal. In FIG. 3c, the overlapping is performed twice, resulting in a signal that is a quarter as long as the original signal. In FIG. 3d, the overlapping is performed three times, resulting in a signal that is one eighth as long as the original signal.

Figure 4:
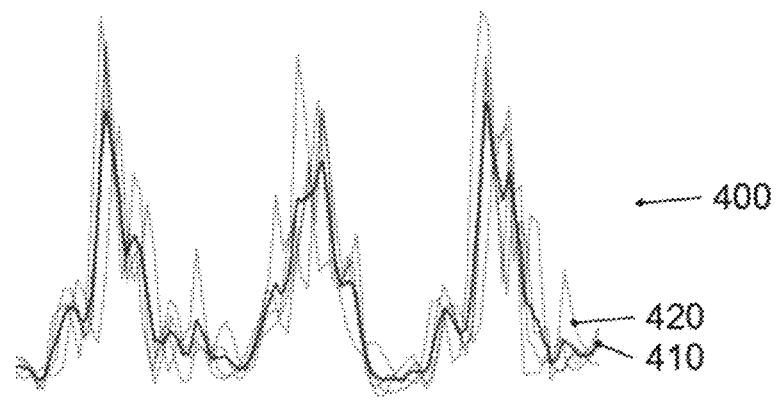
FIG. 4 shows a result of overlapping multiple signals in a combined output signal.

FIG. 4 shows the result of the overlap (e.g. within a combined output signal) according to an embodiment. As shown in FIG. 4, the displayed result of the overlap may comprise the following information—a local average 410 of the signal 400, which is shown as solid line, and local variation 420 of the signal 400, which is shown as dashed lines. The local variation may be displayed as all the periods that were averaged, plotted together with the average, as dashed lines. The locality of the visualization may depend on the number of overlaps. As the number of overlaps increases, the average may reflect the common characteristics of more and more periods (and usually becomes smoother).

Due to the "almost" part of the "almost-periodic signal", during the visualization, the signal may be distorted—neighboring periods may be stretched or compressed in order to become of the exactly same length. This may be seen as a drawback of the method, as it does not visualize the data faithfully. On the other hand, this enables a different view on the signal—this distortion may aim to remove the g function (i.e. the time warp), in order to keep only the periodic part and focus on the repetitive features. Similarly, averaging the signal may aim to remove the n function (i.e. the noise). As a result, the average may be less detailed than the original signal, but in many cases, the removed part is noise, and not an important characteristic.

Figure 5:
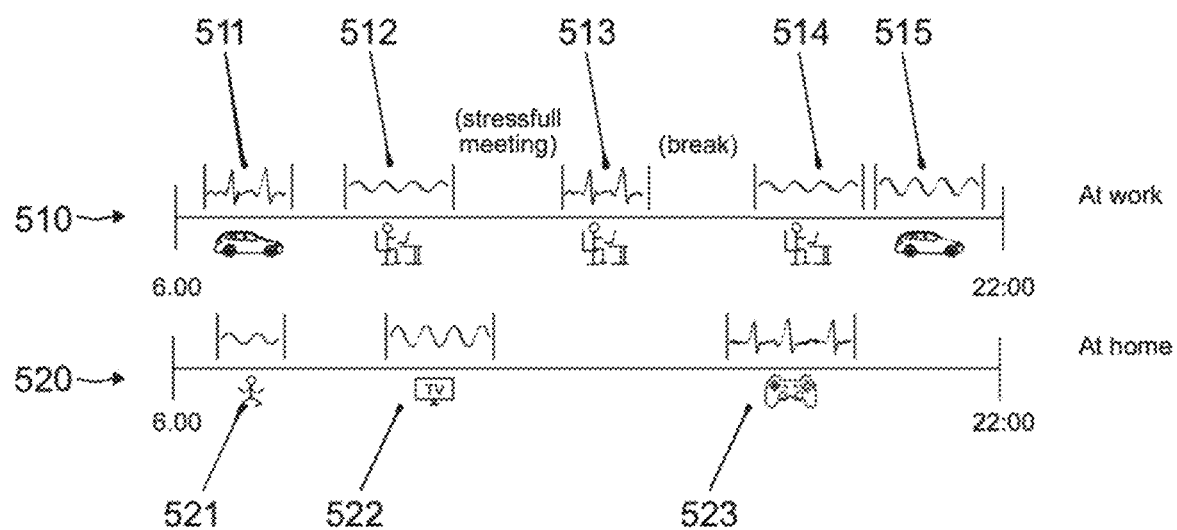
FIG. 5 shows a timeline of different activities of two different days.

In one exemplary application of the concept, an EEG signal may be presented to a user. For a single user, the proposed representation can be consistent for some mental states. The user may learn to recognize and associate the visual expression of the signal with their mental state. FIG. 5 shows an exemplary representation of the EEG signal.

In FIG. 5, two days are displayed, with some intervals when the user wears headphones and the EEG data is available. In these intervals, the meaningful/characteristic representation of EEG is shown. In FIG. 5, a timeline of two days 510 and 520 are shown, the user being at work on one day 510, and at home the other 520. For each day, activities are shown on the bottom, next to an associated EEG signal that is shown on top. For example, for the work day, the activities "driving to work" 511, "working at desk" 512, "working at desk" 513 (with a stressful meeting in between), after a break, "working at desk" 514, and "driving home" are shown. For the day at home, the activities "meditation" 521, "watching television" 522, and "gaming" 523 are shown. As is visible in FIG. 5, each activity may have a characteristic EEG pattern, with some of the patterns being influenced by the activities that have taken place beforehand. For example, the EEG signal of "working at desk" may be different, depending on whether it occurred in the morning or in the afternoon, before or after a stressful meeting, before or after a break etc. Seeing this representation, the user can learn to make associations like "morning commute was stressful, as was the meeting". "I was probably tired in the end of the day". "Deep work is similar to meditation", etc.

To get to the overlapped signal, two tasks may be performed—the time distortion function g may be estimated, and the signal may be overlapped. In embodiments, this may be performed by adjusting a duration of at least a subset of the signal portions such that the signal portions of a set have the same duration, and by superimposing the two or more signal portions of a set within a combined output signal.

Figure 6:
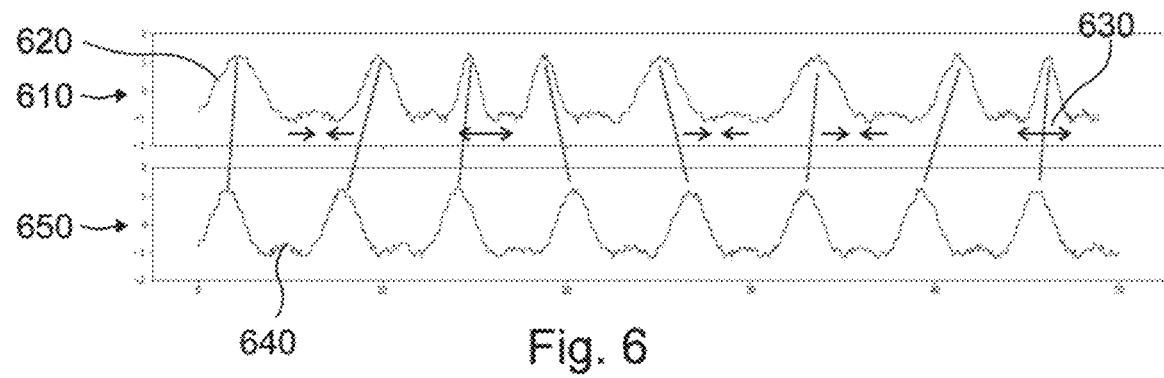
FIG. 6 shows a schematic diagram of an adjustment of a duration of signal portions of an almost-periodic signal.

In the following, it is shown how the function g can be determined, so that the periodic parts of the original signal can be computed (g(x), g(x+p), g(x+2p) . . . ). This may be achieved by locally shrinking or expanding the time axis, as illustrated in FIG. 6. In other words, the duration of the signal portions may be performed by locally shrinking or expanding the time axis of the signal portions. FIG. 6 shows a schematic diagram of an adjustment of a duration of signal portions of an almost-periodic signal. In the upper part 610 of FIG. 6, the almost-periodic signal 620 is shown. The time axis may be locally shrunk or expanded (illustrated by converging or diverging pairs of arrows 630), until the signal 640 becomes periodic (as shown in the lower part 650 of FIG. 6). These local distortions may then be used to compute g.

An exemplary technique to find the appropriate time deformation can be summarized as follows. The time axis may be partitioned into a grid, according to the granularity of the data. Each cell of the grid may be assigned a stretch parameter, which may expand the cell if positive, and contract if negative. This results in a list of grid stretch parameters $c_1, \ldots, c_n$. Also, an additional parameter p represents the period (i.e. the portion) of the periodic sequence, which may be obtained after warping the time. The parameters $c_1, \ldots, c_n$ and p may be optimized/improved simultaneously, e.g. by performing gradient descent on a (specially designed) loss function.

The (specially designed) loss function may comprise or consist of two parts—one that measures a periodicity of the resulting signal, and a second that measures the total amount of stretching required. In detail: In an exemplary implementation, it may be assumed that the chosen grid is the unit grid of length n (that is, intervals [0,1), [1, 2), . . . , [n−1, n)). Grid stretch parameters $c_1, \ldots, c_n$ may be made positive and normalized:

$$c_i^* = \frac{\exp(c_i)}{[\exp(c_1) + \ldots + \exp(c_n)]} \cdot n$$

Function g may then be estimated at a point x as the sum of the stretched grid elements that cover [0, x):

$$g(x) = c_1 + \ldots + c_{[x]} + c_{[x]+1} \cdot \{x\}$$

(here [x] denotes the floor function, and {x} denotes the fractional part x−[x]) For such g and period p, the first part of the loss function may be computed as the following quadratic average:

$$\text{periodicity}_{loss} = \sum_{i=0 \ldots n} ([f(g(i)) - f(g(i+p))]^2)^{\frac{1}{2}}$$

The second part of the loss function may limit the magnitudes of the stretches:

$$\text{stretches\_loss} = \sum_{i=0 \ldots n} \exp(|c_i|).$$

Figure 7A:
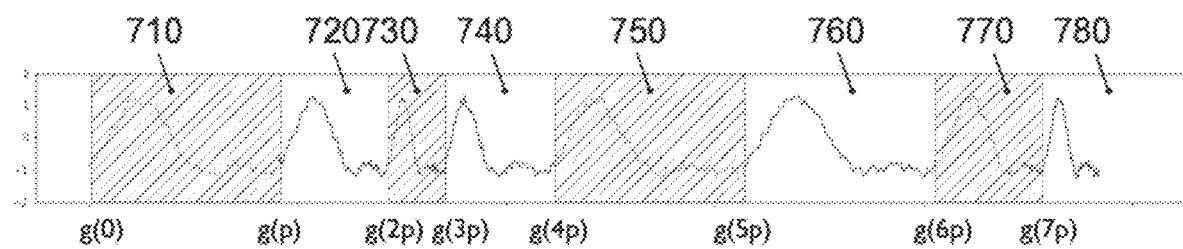
FIGS. 7a to 7d show schematic diagrams of an approach for visualizing an almost-periodic signal.
Figure 7B:
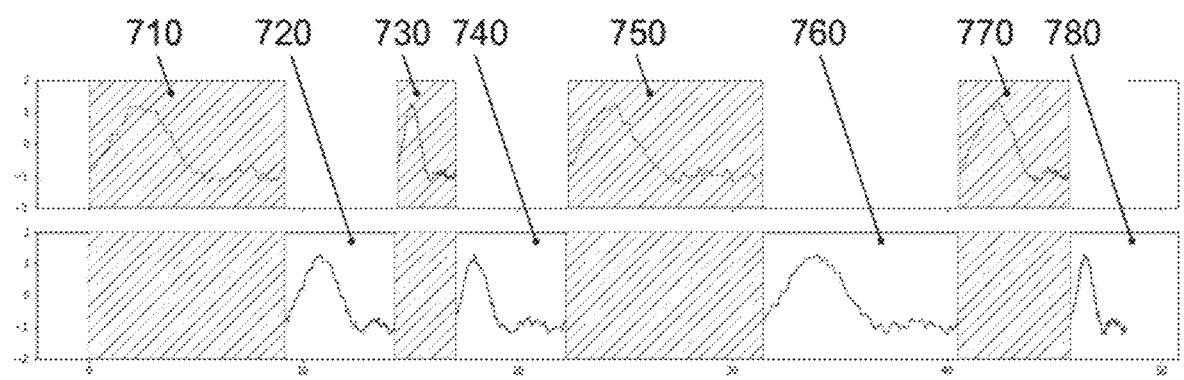
Figure 7C:
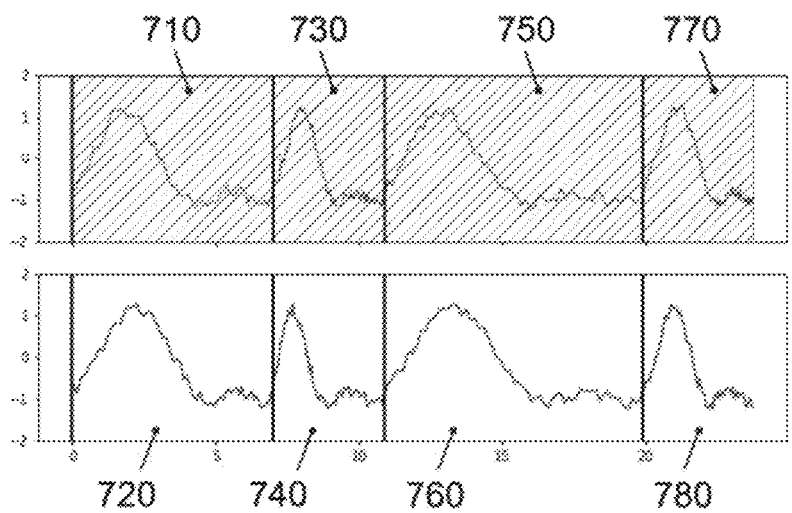
Figure 7D:
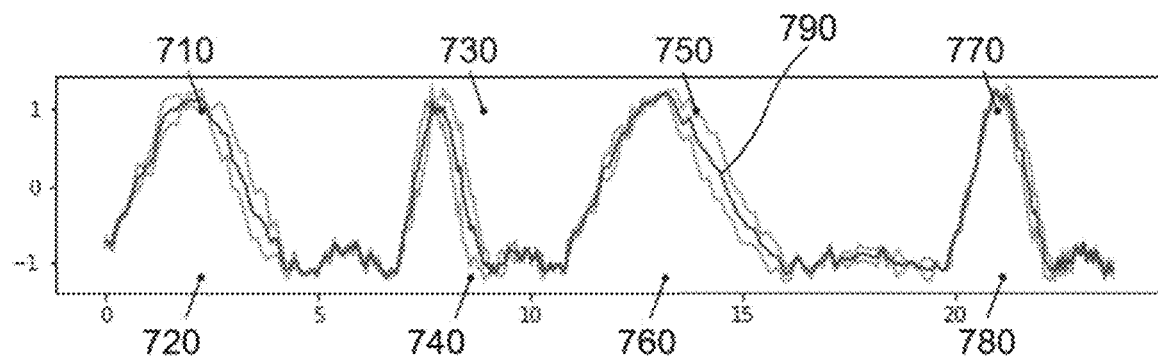

In embodiments, the loss function to reduce/minimize may be the sum of the periodicity$_{loss}$ and stretches$_{loss}$. Embodiments may be used to visualize the (almost) periodic signal. FIGS. 7a to 7d show schematic diagrams of an approach for visualizing an almost-periodic signal. After the function g (with a corresponding period p) has been computed, the signal may be divided into periodic parts, by computing g(0), g(p), g(2p), . . . , as shown in FIG. 7a. Subsequently, two sets of intervals may be selected out of the original sequence—even periods 720, 740, 760, 780, and odd periods 710, 730, 750, 770, and split into two timelines, as shown in FIG. 7b. Subsequently, the even parts and the odd parts may be pushed together, as shown in FIG. 7c, and the lengths of corresponding segments may be equalized (by stretching and squeezing to average). Subsequently, as shown in FIG. 7d, the two separate sequences may be visualized on top of one another (i.e. superimposed on each other), e.g. with a transparency set to ½. Furthermore, the mean 790 may be drawn. This procedure can then be repeated as needed.

Figure 8:
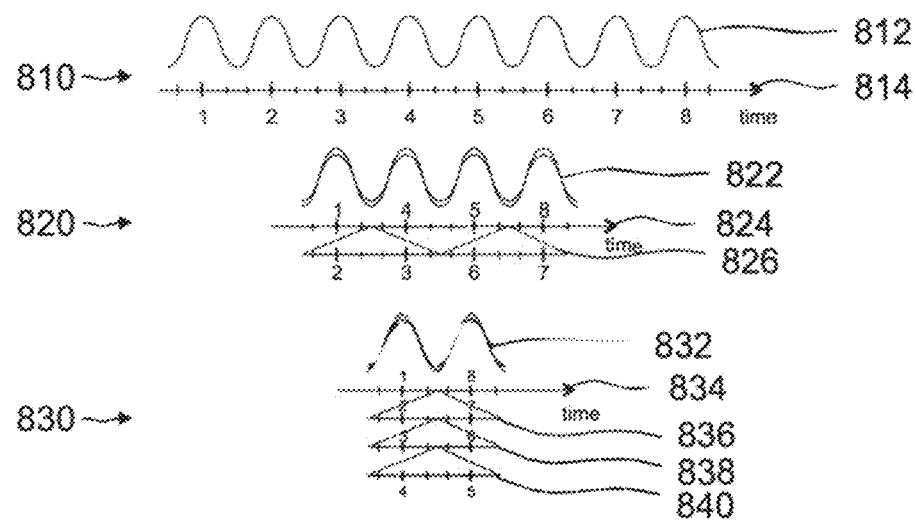
FIG. 8 shows schematic diagrams of an approach for visualizing a time-line in a visualization of an almost-periodic signal.

In order to convey both the scale and the total duration, the same overlapping may be applied to the time axis, as well, as shown in FIG. 8. In FIG. 8 810, the original signal 812 is shown on a time-axis 814 (comprising periods 1 through 8). If the signal uses overlapping (once), as shown with reference to 820, the overlapped signals 822 may be shown, together with an upper time axis 824 comprising half of the periods, and a lower time axis comprising half of the periods. In this example, the upper time axis 824 references periods 1, 4, 5 and 8, and lower time-axis references periods 2, 3, 6, 7. If the procedure is repeated, as shown with reference to 830, such that four periods 832 are overlaid each, four time-axes 834 may be shown. As shown by the dotted lines, the time-axes may be visualized such, that the order of the periods becomes clear from the layout of the time-axes, e.g. by showing, how the time-axes relate to each other (in the original signal).

More details and aspects of the concept are mentioned in connection with the proposed concept or one or more examples described above or below (e.g. FIG. 1a to 1b). The concept may comprise one or more additional optional features corresponding to one or more aspects of the proposed concept or one or more examples described above or below.

The following examples pertain to further embodiments:

(1) A method for processing an almost-periodic input signal comprising a plurality of signal portions of varying duration, the plurality of signal portions being characterized by a common signal shape, the method comprising:
  assigning 110 the plurality of signal portions to a plurality of sets of signal portions, each set of signal portions comprising two or more signal portions;
  adjusting 120 a duration of at least a subset of the signal portions such that the signal portions of a set have the same duration; and
  superimposing 130 the two or more signal portions of a set within a combined output signal.

(2) The method according to (1), wherein the signal portions of a set occur sequentially within the input signal.

(3) The method according to one of (1) or (2), wherein the adjusted duration of the signal portions is the same for the plurality of signal portions.

(4) The method according to one of (1) to (3), wherein the sets of signal portions comprise at least a first set and a second set, the signal portions of the first set having an adjusted duration being different from an adjusted duration of the signal portions of the second set.

(5) The method according to one of (1) to (4), wherein the adjusted duration of the signal portions of a set is based on an average of the durations of the signal portions of the set.

(6) The method according to one of (1) to (5), wherein a fixed number of subsequent signal portions is assigned to the same set.

(7) The method according to one of (1) to (6), wherein the duration of at least the subset of signal portions is adjusted based on a result of a loss function, the loss function being based on a difference between duration-adjusted versions of the signal portions.

(8) The method according to one of (1) to (7), wherein machine-learning is used to vary one or more input parameters of the loss function in order to improve the result of the loss function.

(9) The method according to one of (1) to (8), wherein the input signal is a continuous input signal.

(10) The method according to (9), wherein the adjustment of the duration of the at least subset of the signal portions is based on a portion of the continuous input signal having a pre-defined duration.

(11) The method according to one of (1) to (10), wherein the combined output signal comprises, for each set, the individual signal portions and an average of the signal portions of the set.

(12) The method according to one of (1) to (11), wherein the combined output signal is provided to a visual output device.

(13) The method according to one of (1) to (12), wherein the combined output signal is configured such that the two or more signal portions of a set are shown superimposed over each other on the visual output device.

(14) The method according to (13), wherein the combined output signal is configured such that an average of the signal portions of the set is shown superimposed over the individual signal portions on the visual output device.

(15) The method according to one of (13) or (14), wherein the combined output signal is configured such that a sequence of sets of signal portions is shown on the visual output device.

(16) The method according to one of (1) to (15), wherein the input signal is one of an electroencephalogram signal, an electrocardiogram signal and a photoplethysmogram signal.

(17) The method according to one of (1) to (16), wherein the input signal represents an inertial recording of human movement.

(18) The method according to one of (1) to (17), comprising determining, based on the signal shape or duration of the plurality of signal portions, whether the input signal is quasi-periodic for a portion of the input signal comprising the plurality of signal portions.

(19) A computer program having a program code for performing the method of one of (1) to (18), when the computer program is executed on a computer, a processor, or a programmable hardware component.

(20) An apparatus 10 for processing an almost-periodic input signal comprising a plurality of signal portions of varying duration, the plurality of signal portions being characterized by a common signal shape, the apparatus comprising processing circuitry 14 being configured to:
obtain the almost-periodic input signal;
assign the plurality of signal portions to a plurality of sets of signal portions, each set of signal portions comprising two or more signal portions;
adjust a duration of at least a subset of the signal portions such that the signal portions of a set have the same duration; and superimpose the two or more signal portions of a set within a combined output signal.

(21) The apparatus according to (20), wherein the processing circuitry is configured to provide the combined output signal to a visual output device 20.

(22) A system 100 comprising the apparatus 10 according to (21) and the visual output device 20, wherein the visual output device is configured to output a visual representation of the combined output signal.

The aspects and features mentioned and described together with one or more of the previously detailed examples and figures, may as well be combined with one or more of the other examples in order to replace a like feature of the other example or in order to additionally introduce the feature to the other example.

Examples may further be or relate to a computer program having a program code for performing one or more of the above methods, when the computer program is executed on a computer or processor. Steps, operations or processes of various above-described methods may be performed by programmed computers or processors. Examples may also cover program storage devices such as digital data storage media, which are machine, processor or computer readable and encode machine-executable, processor-executable or computer-executable programs of instructions. The instructions perform or cause performing some or all of the acts of the above-described methods. The program storage devices may comprise or be, for instance, digital memories, magnetic storage media such as magnetic disks and magnetic tapes, hard drives, or optically readable digital data storage media. Further examples may also cover computers, processors or control units programmed to perform the acts of the above-described methods or (field) programmable logic arrays ((F)PLAs) or (field) programmable gate arrays ((F)PGAs), programmed to perform the acts of the above-described methods.

The description and drawings merely illustrate the principles of the disclosure. Furthermore, all examples recited herein are principally intended expressly to be only for illustrative purposes to aid the reader in understanding the principles of the disclosure and the concepts contributed by the inventor(s) to furthering the art. All statements herein reciting principles, aspects, and examples of the disclosure, as well as specific examples thereof, are intended to encompass equivalents thereof.

A functional block denoted as "means for . . . " performing a certain function may refer to a circuit that is configured to perform a certain function. Hence, a "means for s.th." may be implemented as a "means configured to or suited for s.th.", such as a device or a circuit configured to or suited for the respective task.

Functions of various elements shown in the figures, including any functional blocks labeled as "means", "means for providing a signal", "means for generating a signal.", etc., may be implemented in the form of dedicated hardware, such as "a signal provider", "a signal processing unit", "a processor", "a controller", etc. as well as hardware capable of executing software in association with appropriate software. When provided by a processor, the functions may be provided by a single dedicated processor, by a single shared processor, or by a plurality of individual processors, some of which or all of which may be shared. However, the term "processor" or "controller" is by far not limited to hardware exclusively capable of executing software, but may include digital signal processor (DSP) hardware, network processor, application specific integrated circuit (ASIC), field programmable gate array (FPGA), read only memory (ROM) for storing software, random access memory (RAM), and nonvolatile storage. Other hardware, conventional and/or custom, may also be included.

A block diagram may, for instance, illustrate a high-level circuit diagram implementing the principles of the disclosure. Similarly, a flow chart, a flow diagram, a state transition diagram, a pseudo code, and the like may represent various processes, operations or steps, which may, for instance, be substantially represented in computer readable medium and so executed by a computer or processor, whether or not such computer or processor is explicitly shown. Methods disclosed in the specification or in the claims may be implemented by a device having means for performing each of the respective acts of these methods.

It is to be understood that the disclosure of multiple acts, processes, operations, steps or functions disclosed in the specification or claims may not be construed as to be within the specific order, unless explicitly or implicitly stated otherwise, for instance for technical reasons. Therefore, the disclosure of multiple acts or functions will not limit these to a particular order unless such acts or functions are not interchangeable for technical reasons. Furthermore, in some examples a single act, function, process, operation or step may include or may be broken into multiple sub-acts, -functions, -processes, -operations or -steps, respectively. Such sub acts may be included and part of the disclosure of this single act unless explicitly excluded.

Furthermore, the following claims are hereby incorporated into the detailed description, where each claim may stand on its own as a separate example. While each claim may stand on its own as a separate example, it is to be noted that—although a dependent claim may refer in the claims to a specific combination with one or more other claims—other examples may also include a combination of the dependent claim with the subject matter of each other dependent or independent claim. Such combinations are explicitly proposed herein unless it is stated that a specific combination is not intended. Furthermore, it is intended to include also features of a claim to any other independent claim even if this claim is not directly made dependent to the independent claim.

What is claimed is:

1. A method for processing an almost-periodic input signal comprising a plurality of signal portions of varying duration, the plurality of signal portions being characterized by a common signal shape, the method comprising:
   assigning the plurality of signal portions, individual signal portions each being over a period and the plurality of signal portions together being over hundreds of periods, to a plurality of sets of signal portions, each set of signal portions comprising two or more signal portions;
   searching for a transformation among a plurality of transformations by varying input parameters that reduces a loss function based on the difference between duration-adjusted versions of the signal portions;
   determining the input parameters that reduce the loss function;
   removing a local time warp by using the transformation that reduces the loss function to adjust a duration of periods of at least a subset of the signal portions based on the determined input parameters such that the signal portions of a set have the same duration;
   overlapping the two or more signal portions of a set within the same duration within a combined output signal having a shorter duration than a combined duration of the plurality of signal portions; and
   outputting the combined output signal to a display.

2. The method according to claim 1, wherein the signal portions of a set occur sequentially within the input signal.

3. The method according to claim 1, wherein the adjusted duration of the signal portions is the same for the plurality of signal portions.

4. The method according to claim 1, wherein the sets of signal portions comprise at least a first set and a second set, the signal portions of the first set having an adjusted duration being different from an adjusted duration of the signal portions of the second set.

5. The method according to claim 1, wherein the adjusted duration of the signal portions of a set is based on an average of the durations of the signal portions of the set.

6. The method according to claim 1, wherein a fixed number of subsequent signal portions is assigned to the same set.

7. The method according to claim 1, wherein, for each set of the plurality of sets of signal portion, searching for the transformation includes training a machine-learning model by varying one or more input parameters of the loss function in order to improve the result of the loss function.

8. The method according to claim 1, wherein the input signal is a continuous input signal, the adjustment of the duration of the at least subset of the signal portions being based on a portion of the continuous input signal having a pre-defined duration.

9. The method according to claim 1, wherein the combined output signal comprises, for each set, the individual signal portions and an average of the signal portions of the set.

10. The method according to claim 1, wherein the combined output signal is provided to a visual output device.

11. The method according to claim 10, wherein the combined output signal is configured such that the two or more signal portions of a set are shown superimposed over each other on the visual output device.

12. The method according to claim 11, wherein the combined output signal is configured such that an average of the signal portions of the set is shown superimposed over the individual signal portions on the visual output device.

13. The method according to claim 11, wherein the combined output signal is configured such that a sequence of sets of signal portions is shown on the visual output device.

14. The method according to claim 1, wherein the input signal is one of an electroencephalogram signal, an electrocardiogram signal and a photoplethysmogram signal, or wherein the input signal represents an inertial recording of human movement.

15. The method according to claim 1, comprising determining, based on the signal shape or duration of the plurality of signal portions, whether the input signal is quasi-periodic for a portion of the input signal comprising the plurality of signal portions.

16. A non-transitory computer readable storage medium having a program code that when executed by circuitry cause the circuitry to:
   assign a plurality of signal portions, individual signal portion each being over a period and the plurality of signal portions together being over hundreds of periods, to a plurality of sets of signal portions, each set of signal portions comprising two or more signal portions;
   search for a transformation among a plurality of transformations by varying input parameters that reduces a loss function based on the difference between duration-adjusted versions of the signal portions;
determine the input parameters that reduce the loss function;
remove a local time warp by using the transformation that reduces the loss function to adjust a duration of periods of at least a subset of the signal portions based on the determined input parameters such that the signal portions of a set have the same duration;
overlap the two or more signal portions of a set within the same duration within a combined output signal having a shorter duration than a combined duration of the plurality of signal portions; and
outputting the combined output signal to a display.

17. An apparatus for processing an almost-periodic input signal comprising a plurality of signal portions of varying duration, the plurality of signal portions being characterized by a common signal shape, the apparatus comprising processing circuitry being configured to:
obtain the almost-periodic input signal;
assign the plurality of signal portions, individual signal portions each being over a period and the plurality of signal portions together being over hundreds of periods, to a plurality of sets of signal portions, each set of signal portions comprising two or more signal portions;
search for a transformation among a plurality of transformations by varying input parameters that reduces a loss function based on the difference between duration-adjusted versions of the signal portions;
determine the input parameters that reduce the loss function;
remove a local time warp by using the transformation that reduces the loss function to adjust a duration of periods of at least a subset of the signal portions based on the determined input parameters such that the signal portions of a set have the same duration;
overlap the two or more signal portions of a set within the same duration within a combined output signal having a shorter duration than a combined duration of the plurality of signal portions; and
outputting the combined output signal to a display.

18. The apparatus according to claim 17, further comprising the display, wherein the display is configured to receive the combined output signal and display a visual representation of the combined output signal.

19. The apparatus according to claim 17, wherein the processing circuitry is further configured to train a machine-learning model for each set of the plurality of sets of signal portions by varying one or more input parameters of the loss function to improve the result of the loss function.

20. The non-transitory computer readable storage medium according to claim 16, wherein the circuitry is further configured to train a machine-learning model for each set of the plurality of sets of signal portions by varying one or more input parameters of the loss function to improve the result of the loss function.

* * * * *